United States Patent [19]

Sakai et al.

[11] Patent Number: 5,161,085
[45] Date of Patent: Nov. 3, 1992

[54] MOISTURE SENSITIVE ELEMENT AND METHOD OF MANUFACTURING THE SAME

[75] Inventors: Yoshirou Sakai; Yoshihiko Sadaoka; Masanobu Matsuguchi, all of Ehime; Takaaki Kuroiwa; Tooru Abe, both of Kanagawa, all of Japan

[73] Assignee: Yamatake-Honeywell Co., Ltd., Tokyo, Japan

[21] Appl. No.: 837,059

[22] Filed: Feb. 18, 1992

[30] Foreign Application Priority Data

Feb. 21, 1991 [JP] Japan .................. 3-47452
Feb. 21, 1991 [JP] Japan .................. 3-47453

[51] Int. Cl.⁵ .................. H01G 5/20; G01N 25/64
[52] U.S. Cl. .................. 361/286; 73/336.5
[58] Field of Search .......... 73/336.5; 361/323, 286; 29/25.42; 427/41; 428/411.1

[56] References Cited

U.S. PATENT DOCUMENTS

| 4,920,451 | 4/1990 | Sakai et al. | 361/286 |
| 4,938,995 | 7/1990 | Giordano et al. | 427/41 |
| 5,050,434 | 9/1991 | Demisch | 73/336.5 |
| 5,108,840 | 4/1992 | Mercer | 428/411.1 |

Primary Examiner—Donald Griffin
Attorney, Agent, or Firm—Blakely, Sokoloff, Taylor & Zafman

[57] ABSTRACT

A moisture sensitive element includes a moisture sensitive film consisting of a polymer obtained by polymerizing and crosslinking a fluorine-containing polyimide oligomer or a polyisoimide oligomer having acetylene as a terminal group and its isomer. The moisture sensitive element also includes electrodes formed on upper and lower surfaces of the moisture sensitive film.

8 Claims, 7 Drawing Sheets

MOISTURE SENSITIVE ELEMENT AND METHOD OF MANUFACTURING THE SAME

BACKGROUND OF THE INVENTION

The present invention relates to a moisture sensitive element and a method of manufacturing the same and, more particularly, to a capacitive moisture sensitive element having a moisture sensitive film consisting of an organic polymer resin and a method of manufacturing the same.

In conventional moisture sensitive elements of this type, an organic polymer such as cellulose acetate butyrate, cellulose acetate propionate, polyimide, or linear polyamide obtained by polymerizing a linear high-molecular weight polyamic acid is used as a moisture sensitive material. Japanese Patent Laid-Open No. 62-88951, for example, discloses a moisture sensitive element utilizing a change in capacitance of a moisture sensitive film consisting of the above moisture sensitive material to detect a humidity.

A moisture sensitive element having the above structure, however, is highly hydrophilic (i.e., the nature having an affinity for absorbing water), i.e., has a high water absorbing rate. A large amount of water strongly bonded to a polymer by chemical or physical adsorption is left in the moisture sensitive element. For this reason, when a moisture sensitive element is used for a long period of time at a high temperature (e.g., about 40° C.) and a high humidity (e.g., about 90%), long-term stability is undesirably degraded, which results in drifting its output value. A difference (hysteresis) in moisture sensitive characteristics between the humidification and dehumidification processes is small at room temperatures, but is large at low temperatures, thus prolonging the response time. In addition, when a moisture sensitive element is used at a low humidity for a long period of time, the hysteresis is undesirably increased. Output values drift due to the occurrence of moisture condensation and water immersion. When a moisture sensitive element is exposed in an organic solvent, its output value drifts. When a moisture sensitive element has temperature dependent characteristics, they must be corrected with a heat-sensitive element (i.e., a temperature sensor).

SUMMARY OF THE INVENTION

It is, therefore, a principal object of the present invention to provide a moisture sensitive element having a small hysteresis and a high response speed within application ranges from low temperatures to high temperatures and from low humidities to high humidities, and a method of manufacturing the moisture sensitive element.

It is another object of the present invention to provide a moisture sensitive element capable of providing stable output values even if it is left for a long period of time under the following conditions, i.e., even if it is exposed at a high humidity or at a high humidity and a high temperature for a long period of time, left to stand at a low humidity for a long period of time, or exposed in an organic solvent or under conditions such as moisture condensation and water immersion, and a method of manufacturing the moisture sensitive element.

It is still another object of the present invention to provide a moisture sensitive element which has low temperature dependency and is free from temperature correction.

In order to achieve the above objects according to an aspect of the present invention, there is provided a moisture sensitive sensor having a moisture sensitive film formed by using a crosslinked polymer obtained by polymerizing and crosslinking a fluorine-containing polyimide oligomer.

According to another aspect of the present invention, there is provided a method of manufacturing a moisture sensitive element using a moisture sensitive film obtained in such a manner that a fluorine-containing polyimide oligomer is used as a starting material to form a thin film, and the thin film is heat-treated in a nitrogen atmosphere at a temperature of 200° C. or more.

According to still another aspect of the present invention, there is provided a moisture sensitive element having a moisture sensitive film formed by using a polyimide oligomer having acetylene as a terminal group and a polymer obtained by polymerizing an isomer of the above oligomer.

According to still another aspect of the present invention, there is provided a method of manufacturing a moisture sensitive element having a moisture sensitive film obtained such that a polyimide oligomer having acetylene as a terminal group and its isomer are used as starting materials to form a thin film, and the thin film is heat-treated in a nitrogen atmosphere at a temperature of 200° C. or more.

BRIEF DESCRIPTION OF THE DRAWINGS

FIG. 1b is a plan view of the moisture sensitive element shown in FIG. 1a;

DESCRIPTION OF THE PREFERRED EMBODIMENTS

Preferred embodiments of the present invention will be described in detail with reference to the accompanying drawings.

Figure 1A:
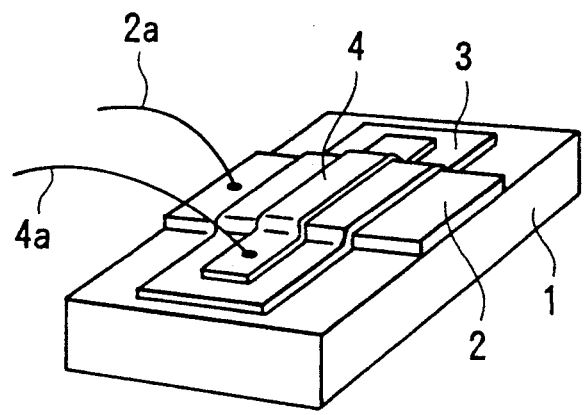
FIG. 1a is a perspective view for explaining the structure of a moisture sensitive element according to an embodiment of the present invention.
Figure 1B:
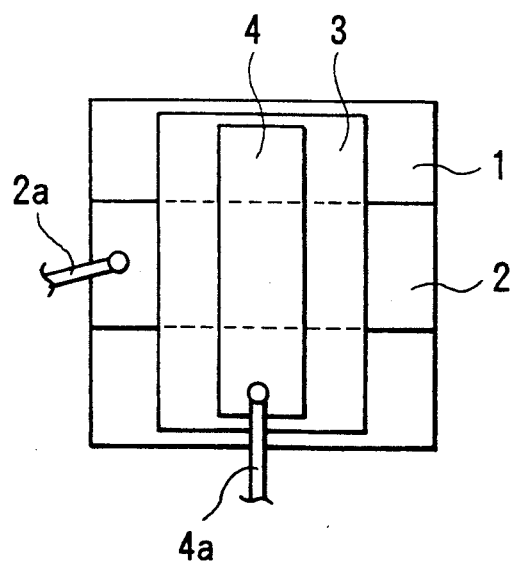

FIGS. 1a and 1b show a structure of a moisture sensitive element according to an embodiment of the present invention. Referring to FIGS. 1a and 1b, reference numeral 1 denotes an insulating substrate such as an alumina substrate, a glass substrate, or a silicon substrate with thermal oxide; 2, a lower electrode consisting of, e.g., platinum formed on the upper surface of the insulating substrate 1; and 3, a moisture sensitive film stacked on and across the lower electrode 2. The moisture sensitive film 3 is made of a moisture sensitive material obtained by polymerizing and crosslinking a fluorine-containing polyimide oligomer. Reference numeral 4 denotes an upper electrode consisting of, e.g., gold, and formed on the moisture sensitive film 3. In this moisture sensitive element, the moisture sensitive film 3 is sandwiched between the lower and upper electrodes 2 and 4, and a change in capacitance corresponding to a relative humidity of the moisture sensitive film 3 is extracted by lead wires 2a and 4a respectively connected to the lower and upper electrodes 2 and 4.

A method of manufacturing this moisture sensitive element will be described below.

5 to 10 g of a fluorine-containing polyimide oligomer powder are prepared and dissolved in 10 to 50 ml of, e.g., diethylene glycol dimethyl ether to obtain a fluorine-containing polyimide oligomer solution. This fluorine-containing polyimide oligomer solution is applied to the surface of the lower electrode 2 formed on the insulating substrate 1 by spin coating and is dried in air or a nitrogen atmosphere at a temperature of 130° to 150° C. for 0.5 to 1.0 hour to obtain the moisture sensitive film having a thickness of 0.1 to 10 μm. At this time, the speed of the spinner is set to fall within a range of 500 to 5,000 rpm. The resultant structure is dried in air or a nitrogen atmosphere, and is then heat-treated in a nitrogen atmosphere at 180° C. for 0.5 to 1 hour, at 230° C. for 1 to 4 hours, and finally at 400° C. for 0.25 to 4 hours, thereby completing polymerization and crosslinking. Note that the fluorine-containing polyimide oligomer has the following chemical formula:

On the insulating substrate 1 having the moisture sensitive film thereon by evaporation, chemical vapor deposition or sputtering, a metal, e.g., gold is deposited to form the upper electrode 4 having a thickness of about 50 to about 1,000 Å. Any metal such as palladium, platinum, or chromium may be used in place of gold as long as it is anti-corrosive. The lower electrode 2 on the insulating substrate 1 is obtained by depositing platinum by evaporation, chemical vapor deposition or sputtering to have a thickness of about 1,000 to about 10,000 Å. A solvent such as tetrahydrofuran, ethylene glycol methyl ether, or N-methylpyrrolidone or a mixture of these solvents may be used in place of diethylene glycol dimethyl ether to obtain the same effect as described above.

Figure 2:
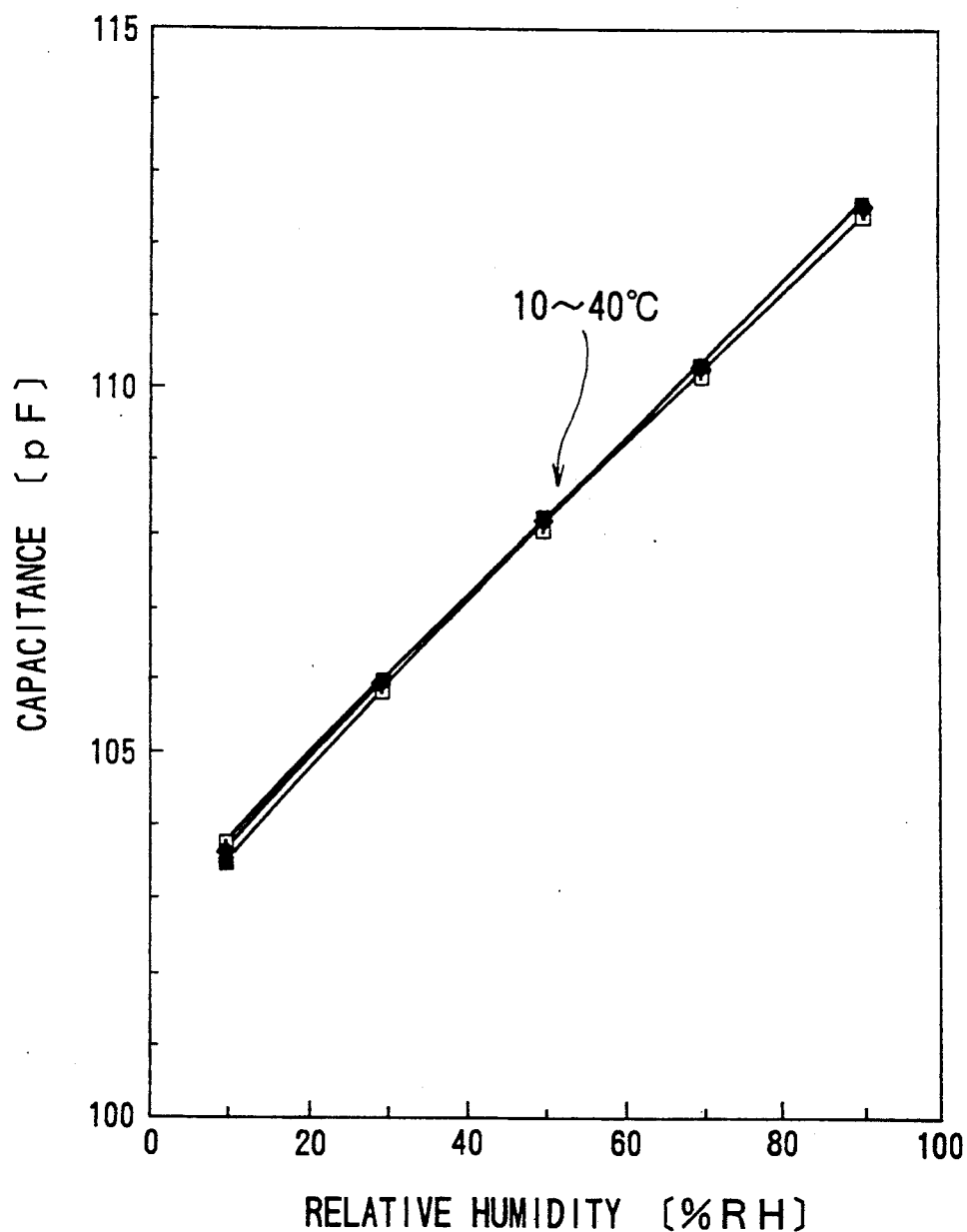
FIG. 2 is a graph showing capacitances of the moisture sensitive element as a function of relative humidities.

As a result of measuring the relative humidity vs. capacitance characteristics of the moisture sensitive element having the above structure, and measured data shown in FIG. 2 were obtained. This measurement was performed using an LCZ meter at a frequency of 100 kHz and temperatures of 10° C., 25° C., and 40° C.

As is apparent from FIG. 2, the moisture sensitive element according to the present invention has low temperature dependency and is excellent in moisture sensitive characteristics. Therefore, it hardly suffers from the influence of temperature changes, and accordingly does not require a temperature correction circuit. As is also apparent from FIG. 2, in a measurement with a lapse of about 2 minutes after the element has been stabilized in a temperature controlled humidity generator or constant temperature oven, a hysteresis is figured out to be 1% RH or less (typically 0.5% RH), thus obtaining desired characteristics.

Figure 3:
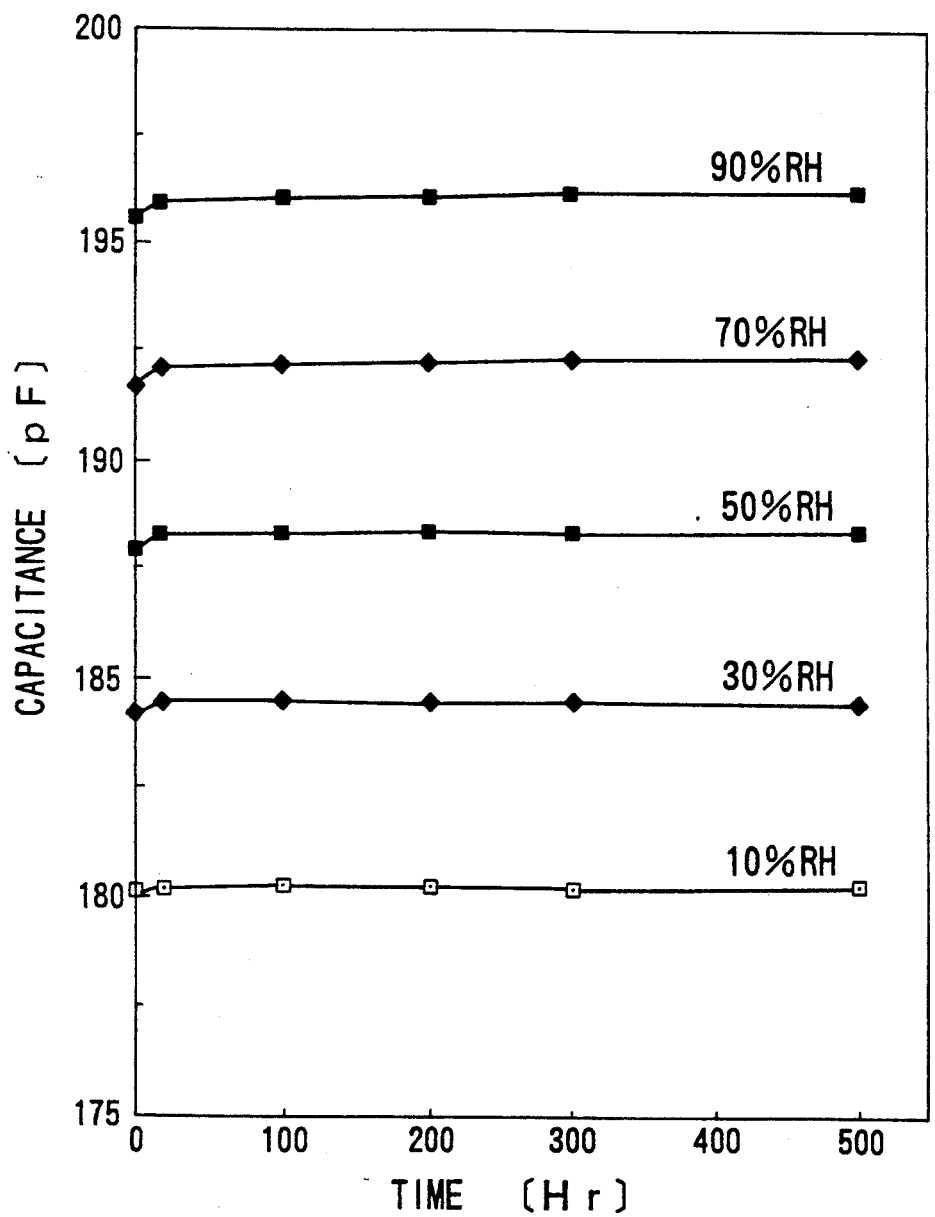
FIG. 3 is a graph showing output drifts at a temperature of 25° C. and relative humidities of 10% RH, 30% RH, 50% RH, 70% RH, and 90% RH after the moisture sensitive element according to the present invention is left at a high temperature and a high humidity.

FIG. 3 shows output drifts at a temperature of 25° C. and relative humidities of 10% RH, 30% RH, 50% RH, 70% RH, and 90% RH after the moisture sensitive element of this embodiment is left at a high temperature (i.e., about 40° C.) and a high humidity (i.e., about 90% RH).

Figure 4:
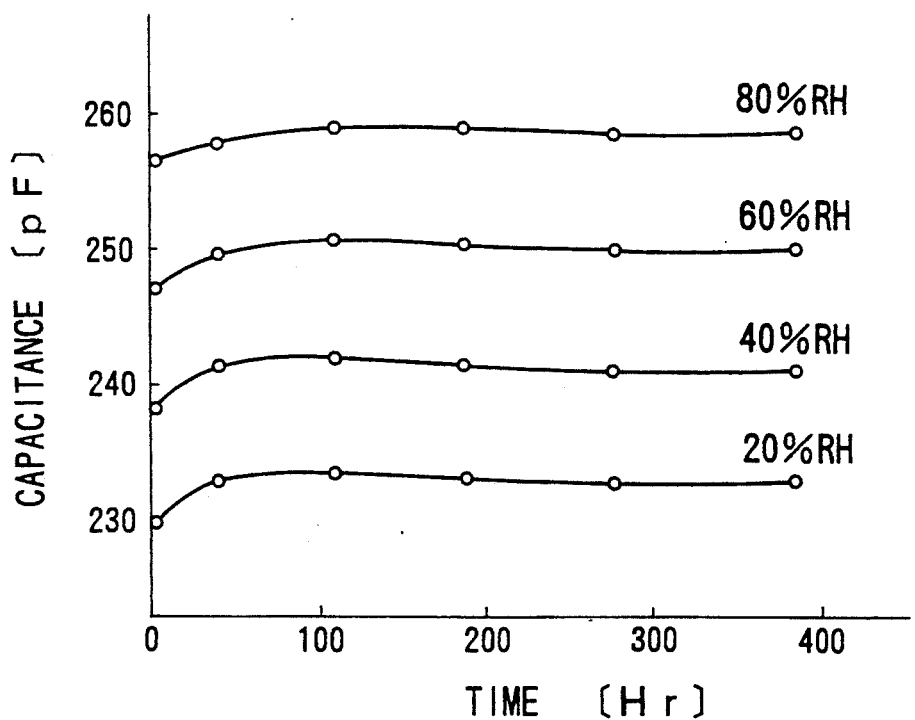
FIG. 4 is a graph showing output drifts at a temperature of 25° C. and relative humidities of 20% RH, 40% RH, 60% RH, and 80% RH after a conventional moisture sensitive element is left at a high temperature and a high humidity.

FIG. 4 shows output drifts of a conventional moisture sensitive element as a comparative example at a temperature of 25° C. and relative humidities of 20% RH, 40% RH, 60% RH, and 80% RH, wherein this moisture sensitive element has a moisture sensitive film consisting of a conventional strip polyimide moisture sensitive material obtained by polymerizing high-molecular

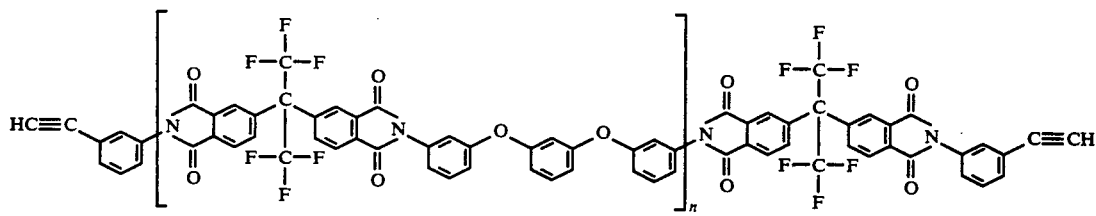

wherein an average degree of polymerization is defined by a repetition count n within the brackets. The average degree n of polymerization falls within a range of 1 to 30. Any material having one of the average degrees n of polymerization falling within the above range can be used as a starting material. The starting material may be a mixture of two or more materials having different average degrees of polymerization.

In the above formula, fluorine is contained to improve hydrophobic properties, thereby a water adsorption can be kept low by fluorine.

weight polyamic acid. As is apparent from FIGS. 3 and 4, the output drifts of the moisture sensitive element of this embodiment are smaller than those of the conventional example (FIG. 4) although the measurable humidity range of the former is larger than that of the latter. That is, good moisture sensitive characteristics having small drifts can be obtained. In a measurement with a lapse of about 2 minutes after the element is stabilized in the humidity chamber or a constant temperature oven, the hysteresis is figured out to be 1% RH or less, and reproducibility is better than that of the conventional example. Even if the sensitive element of this embodiment is left in a given atmosphere having a high temperature and a high humidity for a long period of time, a capacitance ratio is not almost changed and is stabilized. The capacitance ratio is defined as a ratio C90/C10 of an output (C90) obtained at 25° C. and 90% RH to an output (C10) obtained at 25° C. and 10% RH. After having been left in a high temperature and high humidity condition, the moisture sensitive element, when returned in a room temperature atmosphere, can reversibly recover its initial characteristics.

The humidity sensitive element of this embodiment, since the moisture sensitive film thereof is formed of a polymer obtained by polymerizing and crosslinking the fluorine-containing polyimide oligomer, presents a low water, a reduced hysteresis, and low temperature dependency thereby removing the necessity of temperature correction. Stable output values can be obtained even if the moisture sensitive element is exposed for a long period of time in conditions such as in a high temperature and/or high humidity atmosphere in an organic solvent atmosphere, or in moisture condensation conditions. According to the method of manufacturing the moisture sensitive element of this embodiment, the fluorine-containing polyimide oligomer is used as a starting material and heat-treated in a nitrogen atmosphere at a temperature of 200° C. or more. The moisture sensitive element manufactured by this method presents a low water adsorption, reduced drifts stable moisture sensitive characteristics free from temperature dependency, and a minimized hysteresis. Also a high response speed can be obtained. In addition, the moisture sensitive element of this embodiment has a low adsorption water content and is less hydrophilic, thereby making it possible to remove conditioning at a constant temperature and a constant humidity and conditioning such as a temperature-relative humidity cycle upon fabrication.

Another embodiment of the present invention will be described below.

Referring to FIGS. 1a and 1b, a moisture sensitive film 3 is made of a moisture sensitive material obtained by polymerizing and crosslinking a polyimide oligomer having acetylene as a terminal group and its isomer. Other constituting elements and materials used are the same as those of the above embodiment. In addition, the layout of other constituting elements is the same as that of the above embodiment.

A method of manufacturing a moisture sensitive element according to the second embodiment will be described below.

5 to 10 g of a powdered polyisomide oligomer having acetylene as a terminal group (hereinafter referred to as a polyisomide oligomer) as an isomer of a polyimide oligomer having acetylene as a terminal group are prepared and dissolved in 10 to 50 ml of, e.g., diethylene glycol dimethyl ether to obtain a polyisomide oligomer solution.

This polyisomide oligomer solution is applied to the surface of a lower electrode 2 formed on an insulating substrate 1 by spin coating and is dried in air or a nitrogen atmosphere at a temperature of 130° to 150° C. for 0.5 to 1.0 hour to obtain the moisture sensitive film having a thickness of 0.1 to 10 μm. At this time, the speed of the spinner is set to fall within a range of 500 to 5,000 rpm. The resultant structure is dried in air or a nitrogen atmosphere, and is then heat-treated in a nitrogen atmosphere at 180° C. for 0.5 to 1 hour, at 230° C. for 1 to 4 hours, and finally at 400° C. for 0.25 to 4 hours, thereby completing polymerization and crosslinking. Note that the polyisomide oligomer has the following chemical formula:

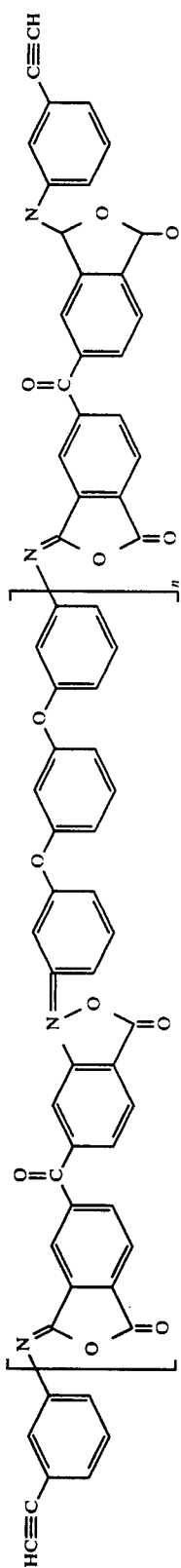

wherein an average degree of polymerization of the polyisomide oligomer is defined by a repetition count n within the brackets. The average degree n of polymerization falls within a range of 1 to 30. Any material having one of the average degrees n of polymerization falling within the above range can be used as a starting material. The starting material may also be a mixture of two or more materials having different average degrees of polymerization.

Next, the insulating substrate 1 having the moisture sensitive film thereon by evaporation, chemical vapor deposition or sputtering, a metal, e.g., gold is deposited to form an upper electrode 4 having a thickness of about 50 to about 1,000 Å. Any metal such as palladium, platinum, or chromium may be used in place of gold as long as it is an anti-corrosive metal. A lower electrode 2 on the insulating substrate 1 is obtained by depositing platinum by evaporation, chemical vapor deposition or sputtering to have a thickness of about 1,000 to about 10,000 Å. A solvent such as tetrahydrofuran, ethylene glycol methyl ether, or N-methylpyrrolidone or a mixture of these solvents may be used in place of diethylene glycol dimethyl ether to obtain the same effect as described above. Note that the starting material in the above fabrication method is not limited to the polyisomide oligomer, but a moisture sensitive element can be manufactured by the above method using a polyimide having acetylene as a terminal group.

Figure 5:
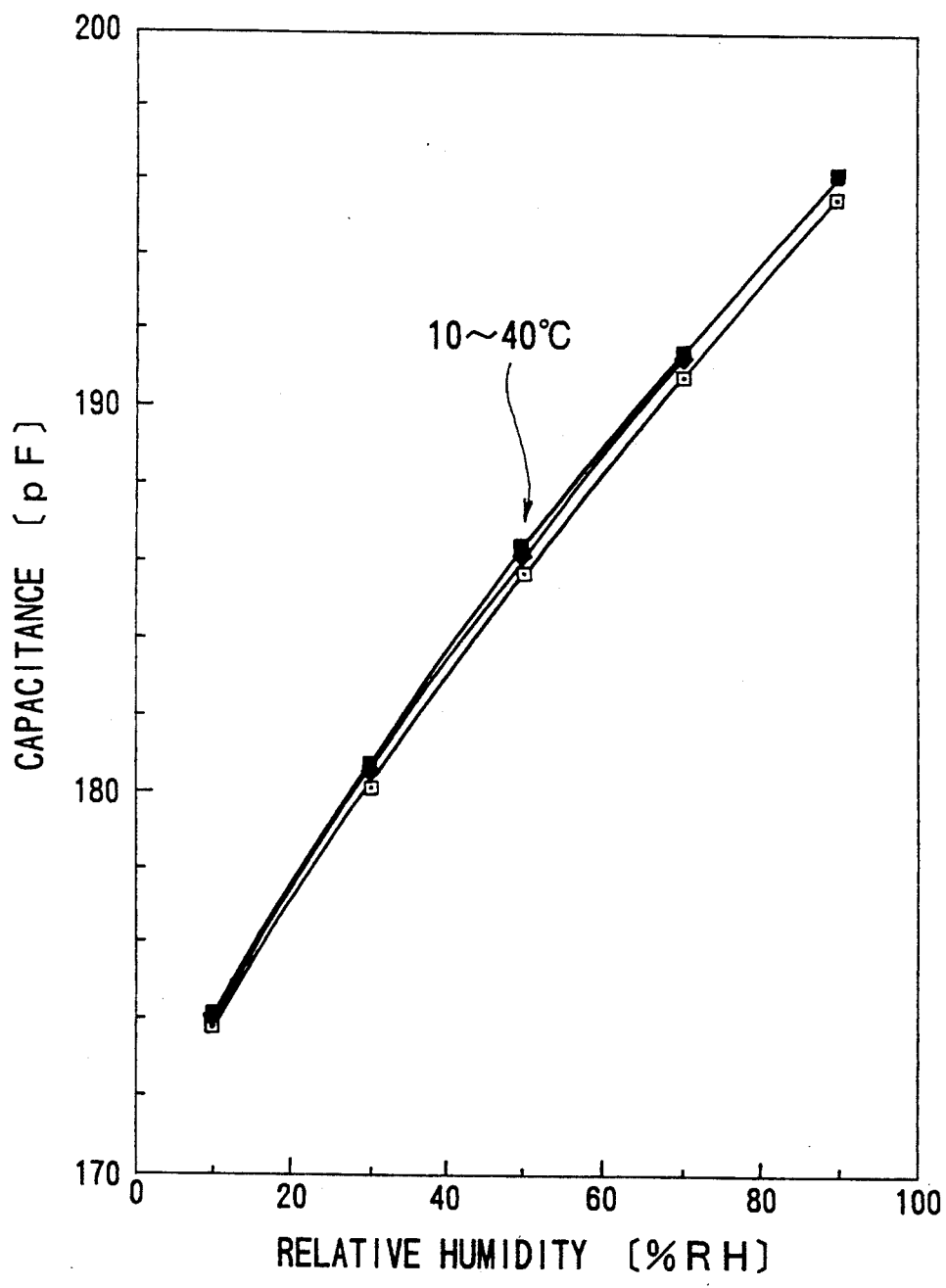
FIG. 5 is a graph showing capacitances of a moisture sensitive element as a function of relative humidities according to another embodiment of the present invention.

As a result of measuring the relative humidity vs. capacitance characteristics of the moisture sensitive element having the above structure, measured data shown in FIG. 5 were obtained. This measurement was performed using an LCZ meter at a frequency of 100 kHz and temperatures of 10° C., 25° C., and 40° C. As is apparent from FIG. 5, the moisture sensitive element according to the present invention has low temperature dependency and is excellent in moisture sensitive characteristics. Therefore, it hardly suffers from the influence of temperature changes and accordingly does not require a temperature correction circuit. As is also apparent from FIG. 5, in a measurement with a lapse of about 2 minutes after the element has been stabilized in a humidity chamber or a constant temperature oven, a hysteresis is figured out to be 1% RH or less, thus obtaining desired characteristics.

Figure 6:
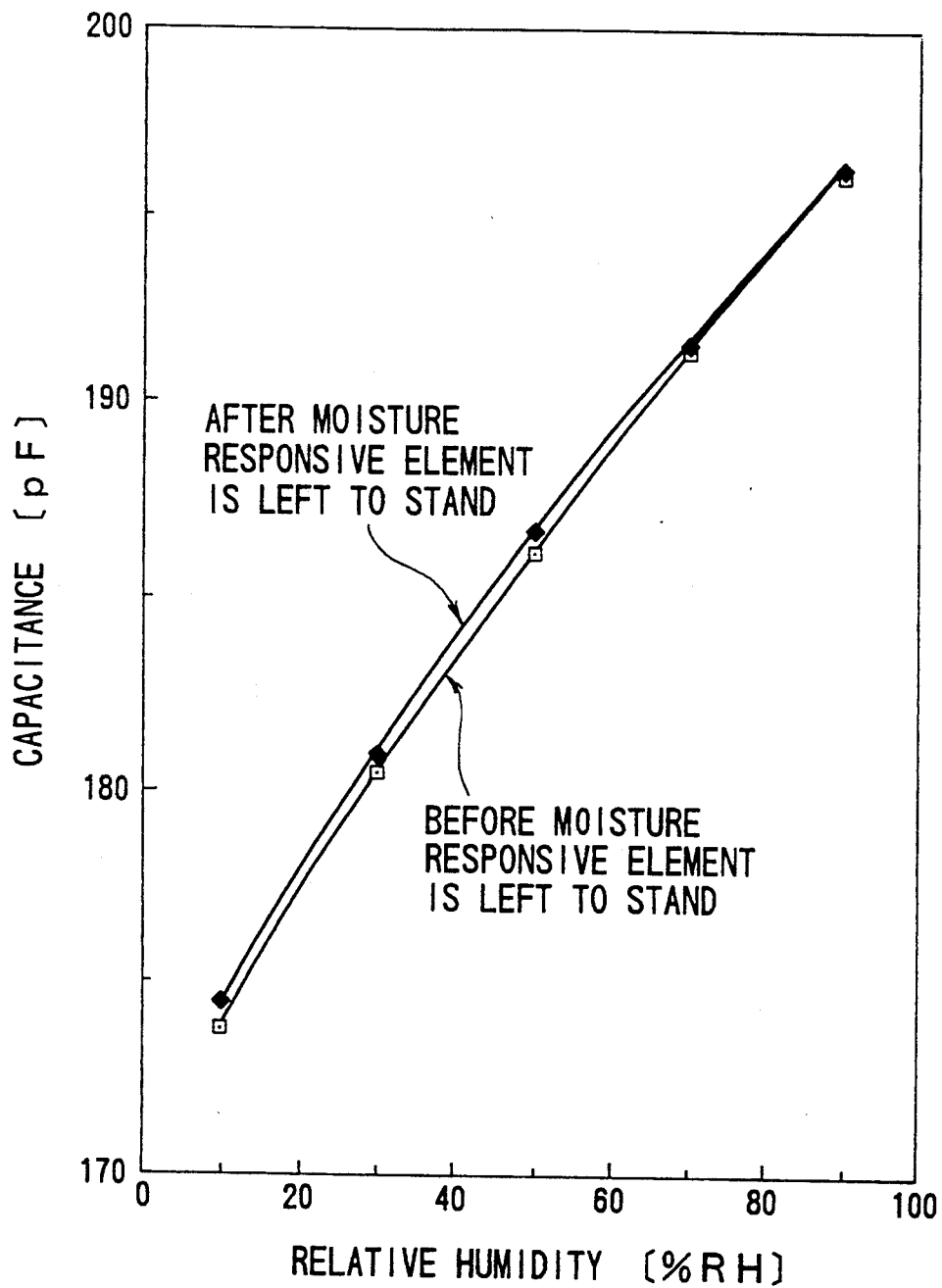
FIG. 6 is a graph showing outputs at a temperature of 25° C. and relative humidities of 10% RH, 30% RH, 50% RH, 70% RH, and 90% RH before and after the moisture sensitive element shown in FIG. 5 is left in an acetone saturated vapor at a room temperature for 20 minutes.

FIG. 6 shows output drifts at a temperature of 25° C. and relative humidities of 10% RH, 30% RH, 50% RH, 70% RH, and 90% RH before and after the moisture sensitive element of this embodiment is left in an acetone saturated vapor for 20 minutes. As is apparent from FIG. 6, no change is found before and after the element is left in the above atmosphere, and stable (small drifts) moisture sensitive characteristics can be obtained.

Figure 7:
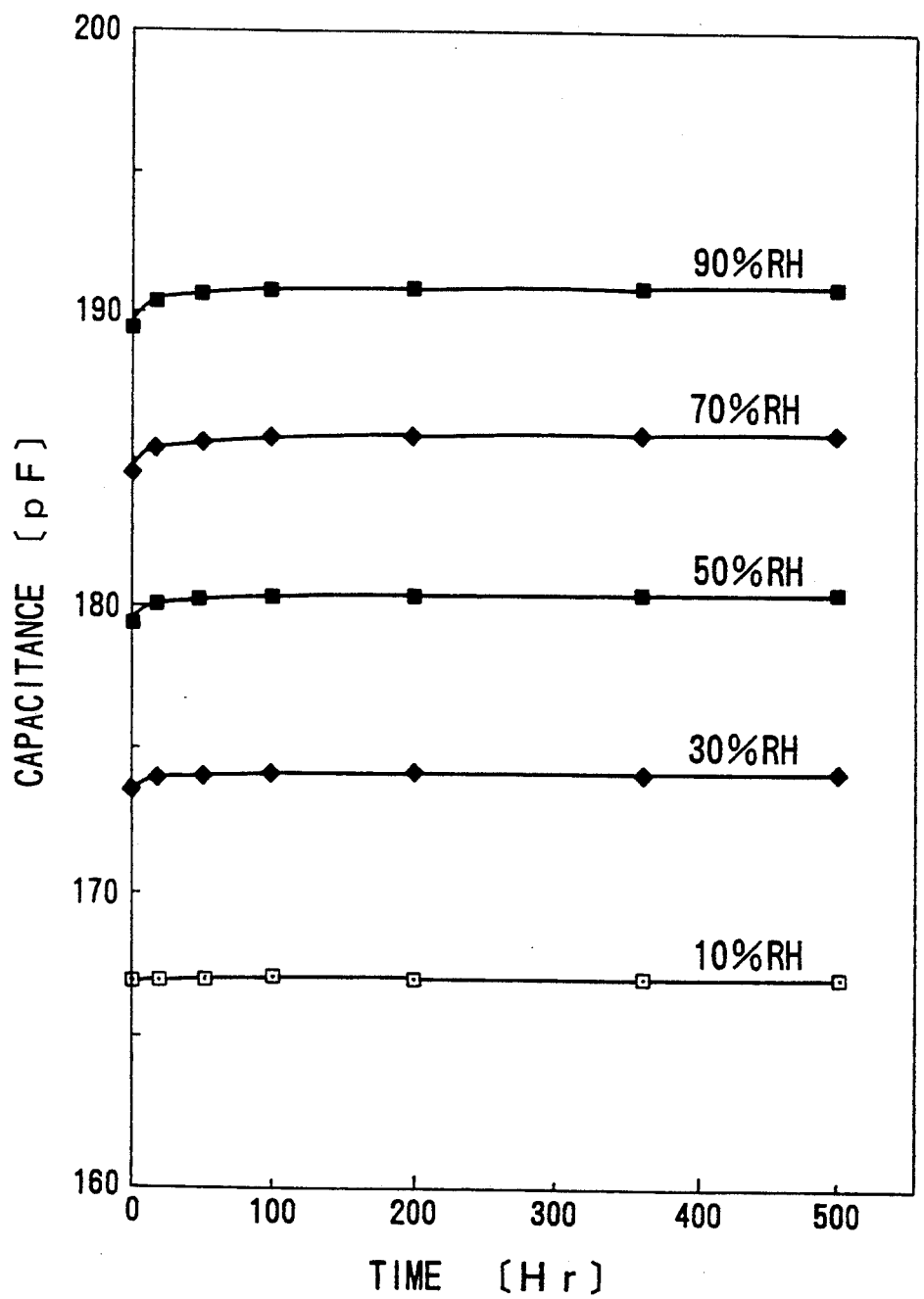
FIG. 7 is a graph showing output drifts at a temperature of 25° C. and relative humidities of 10% RH, 30% RH, 50% RH, 70% RH, and 90% RH after the moisture sensitive element shown in FIG. 5 is left at a high temperature (e.g., about 40° C.) and a high humidity (e.g., about 90% RH).

FIG. 7 shows output drifts of the moisture sensitive element of the this embodiment at a temperature of 25° C. after it is left in a high temperature (i.e., about 40° C.) and a high humidity (i.e., about 90% RH).

When the moisture sensitive element of the second embodiment is compared with the moisture sensitive element having the moisture sensitive film consisting of a polyimide moisture sensitive material obtained by polymerizing the conventional strip-like high-molecular weight polyamic acid. The output drifts of the moisture sensitive element of the second embodiment are smaller than those of the conventional example although its measurable humidity range is wider than that of the conventional example. That is, good moisture sensitive characteristics having small drifts can be obtained. In a measurement with a lapse of about 2 minutes after the element has been stabilized in the humidity chamber or the constant temperature oven, the hysteresis is figured out to be 1% RH or less, and reproducibility is better than that of the conventional example. Even if the moisture sensitive element of this embodiment is left in a given atmosphere having a high temperature and a high humidity for a long period of time, a capacitance ratio is not almost changed and is stabilized. The capacitance ratio is defined as a ratio C90/C10 of an output (C90) obtained at 25° C. and 90% RH to an output (C10) obtained at 25° C. and 10% RH. After having been left in a high temperature and high humidity condition, the moisture sensitive element, when returned in a room temperature atmosphere, can reversibly recover its initial characteristics.

In the above embodiments, although the moisture sensitive elements each having a sandwich structure are exemplified, the present invention is not limited to this. The present invention is also applicable to an interdigital moisture sensitive element in which a pair of interdigital thin-film electrodes may be formed to oppose each other on the surface of an insulating substrate, and a moisture sensitive film is stacked to cover the interdigital thin-film electrodes, thereby obtaining the same effects as in the above embodiments.

In the above embodiments, a humidity is detected on the basis of a change in capacitance caused by a change in relative humidity. However, such humidity detection may be performed on the basis of a change in impedance caused by a change in relative humidity.

The moisture sensitive film of each embodiment described above is also suitable for use in a moisture sensitive element wherein the moisture sensitive film is formed on a quartz oscillator, and a humidity is detected in accordance with a shift of resonance frequency caused by adsorption of moisture in the moisture sensitive film. In addition, the moisture sensitive film of each embodiment described above is further suitable for use in a moisture sensitive element wherein the moisture sensitive film is formed on a surface acoustic wave element, and a humidity is detected in accordance with a change in speed of a wave passing through the surface acoustic wave element.

The moisture sensitive elements of the present invention presents a low water adsorption, a reduced hysteresis, low temperature dependency, thereby removing the necessity of temperature correction. Stable output values can be obtained even if the moisture sensitive element is exposed for a long period of time, in conditions such as in a high temperature and/or high humidity atmosphere, in an organic solvent atmosphere, or under conditions such in moisture condensation conditions. According to the method of manufacturing the moisture sensitive element of the second embodiment, the water adsorption becomes low, the drifts can be minimized. Stable moisture sensitive characteristics free from temperature dependency can be obtained, and the hysteresis can be minimized. A high response speed can be obtained. In addition, since the moisture sensitive element of this embodiment has a low adsorption water content and is less hydrophilic, conditioning in a constant temperature and a constant humidity and conditioning such as a temperature-relative humidity cycle upon fabrication can be eliminated, thus providing excellent industrial advantages.

What is claimed is:
1. A moisture sensitive element comprising:

a moisture sensitive film consisting of a polymer obtained by polymerizing and crosslinking a fluorine-containing polyimide oligomer; and electrodes formed on upper and lower surfaces of said moisture sensitive film.

2. An element according to claim 1, wherein said electrode formed on said lower surface of said moisture sensitive film is formed on an insulating substrate.

3. A method of manufacturing a moisture sensitive element having electrodes on upper and lower surfaces of a moisture sensitive film, comprising the steps of:

using a fluorine-containing polyimide oligomer as a starting material to form a thin film; and heat-treating said thin film in a nitrogen atmosphere at a temperature of not less than 200° C. to form said moisture sensitive film.

4. A method according to claim 3, wherein the starting material comprises an oligomer consisting of at least one mixer of oligomers having average degrees n of polymerization of the fluorine-containing polyimide oligomer to fall within a range of n=1 to n=30.

5. A moisture sensitive element comprising:

a moisture sensitive film consisting of a polymer obtained by polymerizing a polyisoimide oligomer having acetylene as a terminal group and an isomer thereof; and electrodes formed on upper and lower surfaces of said moisture sensitive film.

6. An element according to claim 5, wherein said electrode formed on said lower surface of said moisture sensitive film is formed on an insulating substrate.

7. A method of manufacturing a moisture sensitive element having electrodes on upper and lower surfaces of a moisture sensitive film, comprising the steps of:

using a polyimide oligomer having acetylene as a terminal group and an isomer thereof as starting materials to form a thin film, and heat-treating said thin film in a nitrogen atmosphere at a temperature of not less than 200° C. to form said moisture sensitive film.

8. A method according to claim 7, wherein the starting materials comprise oligomers consisting of at least one mixture of oligomers having average degrees n of polymerization of the polyimide oligomer having acetylene as a terminal group and the isomer thereof to fall within a range of n=1 to n=30.

* * * * *